US012419559B2

United States Patent
Wang et al.

(10) Patent No.: US 12,419,559 B2
(45) Date of Patent: Sep. 23, 2025

(54) SENSOR READOUT CIRCUITRY, A BIOPOTENTIAL SIGNAL SENSOR, A NEURAL PROBE, AND A METHOD FOR READOUT OF AN ANALOG SENSOR INPUT SIGNAL

(71) Applicant: IMEC VZW, Leuven (BE)

(72) Inventors: Shiwei Wang, Leuven (BE); Marco Ballini, Leuven (BE)

(73) Assignee: IMEC VZW, Leuven (BE)

( * ) Notice: Subject to any disclaimer, the term of this patent is extended or adjusted under 35 U.S.C. 154(b) by 864 days.

(21) Appl. No.: 17/693,907

(22) Filed: Mar. 14, 2022

(65) Prior Publication Data

US 2022/0296142 A1 Sep. 22, 2022

(30) Foreign Application Priority Data

Mar. 16, 2021 (EP) ..................................... 21162839

(51) Int. Cl.
*A61B 5/24* (2021.01)
*A61B 5/00* (2006.01)
*A61N 1/05* (2006.01)

(52) U.S. Cl.
CPC .............. *A61B 5/24* (2021.01); *A61B 5/0031* (2013.01); *A61B 5/6868* (2013.01); *A61N 1/0529* (2013.01)

(58) Field of Classification Search
CPC ....... A61B 5/24; A61B 5/0031; A61B 5/6868; A61N 1/0529; H03M 3/34

(Continued)

(56) References Cited

U.S. PATENT DOCUMENTS 4,912,423 A * 3/1990 Milkovic ................ H03F 1/303
330/288
6,697,001 B1 * 2/2004 Oliaei .................... H03M 3/356
327/552

(Continued)

OTHER PUBLICATIONS

An important component in bioimpedance measurements is the current driver, which can operate over a wide range of impedance and frequency. This paper provides a review of integrated circuit analog current drivers which have been developed in the last 10 years. (Year: 2019).*

(Continued)

*Primary Examiner* — Eman A Alkafawi
*Assistant Examiner* — Joseph O Nyamogo
(74) *Attorney, Agent, or Firm* — MOSER TABOADA

(57) ABSTRACT

A sensor readout circuitry comprises: a delta-sigma modulator; an input stage for receiving an analog sensor input signal, wherein a transconductance amplifier and a current mirror incorporate a flipped voltage follower, wherein a feedback signal from a digital-to-analog converter of the delta-sigma modulator is received such that subtraction between the analog sensor input signal and the feedback signal is performed in the transconductance amplifier and mirrored by the current mirror to an output of the input stage; wherein the transconductance amplifier comprises a first, second and third chopper, whereby a chopping loop between the first, second and third choppers is formed including an input transistor and current sources and whereby the analog sensor input signal is in baseband at a node in which the feedback signal is received.

14 Claims, 6 Drawing Sheets

(58) Field of Classification Search
USPC .......................................................... 702/189
See application file for complete search history.

(56) References Cited

U.S. PATENT DOCUMENTS

| 7,098,827 | B2 | 8/2006 | Motz | |
|---|---|---|---|---|
| 2010/0164616 | A1 | 7/2010 | Balachandran | |
| 2017/0041019 | A1* | 2/2017 | Miglani | H03M 1/0626 |
| 2017/0281037 | A1* | 10/2017 | Kidmose | H03F 3/45183 |

OTHER PUBLICATIONS

Motz et al: "16.6 An Integrated Magnetic Sensor with Two Continuous-Time ΔΣ-Converters and Stress Compensation Capability", Digest of Technical Papers, 2006 IEEE International Solid-State Circuits Conference, San Francisco, California, Feb. 5-9, 2006, pp. 1151-1160, 2006.

Van Helleputte et al: "A 160 μA Biopotential Acquisition IC With Fully Integrated IA and Motion Artifact Suppression", IEEE Transactions on Biomedical Circuits and Systems, vol. 6, No. 6, pp. 552-561, 2012.

Billa et al: "Analysis and Design of Continuous-Time Delta-Sigma Converters Incorporating Chopping", IEEE Journal of Solid-State Circuits, vol. 52, No. 9, pp. 2350-2361, 2017.

De Dorigo et al: "Fully Immersible Subcortical Neural Probes With Modular Architecture and a Delta-Sigma ADC Integrated Under Each Electrode for Parallel Readout of 144 Recording Sites", IEEE Journal of Solid-State Circuits, vol. 53, No. 11, pp. 3111-3125, 2018.

Jiang et al: "A 4.5 nV/√Hz Capacitively Coupled Continuous-Time Sigma-Delta Modulator with an Energy-Efficient Chopping Scheme", IEEE Solid-State Circuits Letters, vol. 1, No. 1, pp. 18-21, 2018.

Wang et al: "A Compact Quad-Shank CMOS Neural Probe With 5,120 Addressable Recording Sites and 384 Fully Differential Parallel Channels", IEEE Transactions on Biomedical Circuits and Systems, vol. 13, No. 6, pp. 1625-1634, 2019.

Lee et al: "26.6 A 6.5 μW 10 kHz-BW 80.4dB-SNDR Continuous-Time ΔΣ Modulator with $G_m$-Input and 300mV$_{pp}$ Linear Input Range for Closed-Loop Neural Recording", 2020 IEEE International Solid-State Circuits Conference—(ISSCC), pp. 410-412, 2020.

Extended European Search Report in EP21162839.1 dated Aug. 27, 2021.

* cited by examiner

SENSOR READOUT CIRCUITRY, A BIOPOTENTIAL SIGNAL SENSOR, A NEURAL PROBE, AND A METHOD FOR READOUT OF AN ANALOG SENSOR INPUT SIGNAL

CROSS-REFERENCE TO RELATED APPLICATIONS

This application claims benefit of EP patent application number 21162839.1 filed on Mar. 16, 2021, which is herein incorporated by reference in its entirety.

TECHNICAL FIELD

The present inventive concept relates to a sensor readout circuitry which is configured to convert an analog sensor input signal to a digital signal. The sensor readout circuitry may be used in a biopotential signal sensor, and in particular, in a neural probe. The present inventive concept also relates to a method for readout of an analog sensor input signal.

BACKGROUND

In many sensor applications, a small size of circuitry for acquisition of signals from a sensor is desired. In particular, a small size of the circuitry may be desired in acquisition of biopotential signals, such as in a neural probe, since the sensor is to be worn by or implanted in a subject. A small size of a wearable or implantable device may ensure a low impact on the subject wearing the wearable device or low impact of invasiveness of the implantable device.

Readout circuitry for signal acquisition may be implemented in a delta-sigma modulator, which may provide for a compact circuitry for readout of sensor signals. The delta-sigma modulator provides analog-to-digital conversion of an analog sensor input signal, that is an input signal to the delta-sigma modulator from an analog sensor. The delta-sigma modulator provides a high resolution such that no separate circuitry for amplifying the analog sensor input signal is needed. Also, delta-sigma modulation provides oversampling of the analog sensor input signal, such that no separate anti-aliasing filter may be necessary for noise reduction. In particular, in a continuous-time delta-sigma modulator (CTDSM), the analog sensor input signal passes a loop filter before being sampled, such that the loop filter acts as an anti-aliasing filter.

Hence, a delta-sigma modulator facilitates having a small sensor readout circuitry. However, when impedance of the sensor providing a sensor input signal is high, which in particular is true for small electrodes, signal amplitude will be degraded if the readout circuitry does not provide a high input impedance. In order to achieve a high input impedance, the delta-sigma modulator may be provided with a transconductance amplifier at an input stage of the delta-sigma modulator.

The transconductance amplifier may however be a source of flicker noise in readout of the sensor input signal.

SUMMARY

An objective of the present inventive concept is to provide a sensor readout circuitry using a delta-sigma modulator that may provide high input impedance and good noise performance.

These and other objectives of the present inventive concept are at least partly met by the invention as defined in the independent claims. Preferred embodiments are set out in the dependent claims.

According to a first aspect, there is provided a sensor readout circuitry comprising: a delta-sigma modulator for converting an analog sensor input signal to a digital signal; an input stage for receiving the analog sensor input signal, wherein the input stage comprises a transconductance amplifier comprising a pair of input transistors and a source degeneration resistor, a current mirror, and current sources, wherein the transconductance amplifier and the current mirror incorporate a flipped voltage follower, wherein a feedback signal from a digital-to-analog converter (DAC) of the delta-sigma modulator is received across the source degeneration resistor such that subtraction between the analog sensor input signal and the feedback signal is performed in the transconductance amplifier and mirrored by the current mirror to an output of the input stage; wherein the transconductance amplifier comprises a first chopper between an input terminal for receiving the analog sensor input signal and an input transistor of the pair of input transistors for upmodulating the analog sensor input signal; wherein the transconductance amplifier comprises a second chopper between the input transistor and the source degeneration resistor such that the analog sensor input signal is in baseband at a node in which the feedback signal is received; wherein the transconductance amplifier comprises a third chopper before a connection of the transconductance amplifier to shared gates of the current mirror such that signals in the current mirror are in baseband; whereby a chopping loop between the first, second and third choppers is formed including the input transistor and the current sources.

The sensor readout circuitry provides the first chopper to upmodulate the analog sensor input signal, which enables chopper stabilization to be used for filtering out the flicker noise.

However, it is an insight of the invention that use of chopper stabilization could imply that high-frequency quantization noise may be folded into signal band and degrade noise performance of the readout circuitry. Thanks to the sensor readout circuitry of the first aspect, a chopping loop is created such that chopper stabilization may be utilized while the feedback signal from the DAC is not received within the chopping loop. This implies that any quantization noise is not folded by the chopping loop such that folding of quantization noise into signal band may be avoided.

The chopping loop includes the input transistor and the current sources. It is realized that the input transistor and the current sources are contributors to flicker noise. Hence, thanks to the input transistor and the current sources being arranged within the chopping loop formed by the first, second, and third choppers, the flicker noise from the input transistor and the current sources may be filtered out so as to improve noise performance of the sensor readout circuitry.

The flicker noise of a transistor is inversely dependent on a size of the transistor such that the flicker noise is increased when the transistor size is decreased. Thanks to the chopper stabilization, size of transistors may be reduced without a risk that the flicker noise affects the readout of the analog sensor input signal. Hence, an area of transistors of the sensor readout circuitry may be small, such that the sensor readout circuitry may be provided in a small area.

Thanks to the transconductance amplifier and the current mirror incorporating a flipped voltage follower, an output node of the flipped voltage follower may follow closely a voltage at an input transistor of the pair of input transistors.

The sensor readout circuitry may comprise a first and a second flipped voltage follower each associated with a respective one of the input transistors in the pair of input transistors. The first and the second flipped voltage follower may each comprise an output node, wherein the output nodes of the first and second flipped voltage followers may be arranged on opposite sides of the source degeneration resistor. This implies that the voltage across the source degeneration resistor may follow closely the input signals on the pair of input transistors. Hence, an actual transconductance of the transconductance amplifier is mostly determined by a resistance of the source degeneration resistor and thus high linearity of the input stage may be achieved.

Although the chopping loop is described in relation to one input transistor of the pair of input transistors, it should be realized that a corresponding chopping loop may be formed in relation to the other input transistor as well.

As used herein, the term "analog sensor input signal" should be construed as an input signal to the sensor readout circuitry, wherein the input signal is received from an analog sensor.

According to an embodiment, nodes in which the feedback signal is received are further connected to the current mirror having low impedance such that the circuitry is configured for DAC feedback current to flow into the current mirror and not be affected by chopping by the second chopper.

The current mirror forming part of the flipped voltage follower may be connected to the nodes in which the feedback signal is received. The flipped voltage follower may contribute to low output impedance for current flowing into the current mirror. Thus, the DAC feedback current may flow into the current mirror so as to avoid that the DAC feedback current is chopped by the second chopper. Hence, folding of quantization noise through chopping by the second chopper is avoided.

According to an embodiment, the delta-sigma modulator is a continuous-time delta-sigma modulator (CTDSM).

This implies that an inherent anti-aliasing filter is provided by the CTDSM in the sensor readout circuitry. Hence, there may be no need of an additional anti-aliasing filter in the sensor readout circuitry.

According to an embodiment, the first, second and third choppers are configured to operate at a chopping frequency between a Nyquist rate and a sample rate of the delta sigma modulator.

The first chopper is configured to upmodulate the analog sensor input signal such that a bandwidth of frequencies of interest in the analog sensor input signal are upmodulated to multiples of the chopping frequency by the first chopper. The frequencies of interest may again be downmodulated to baseband by the second chopper, while the modulation by the second chopper may upmodulate low frequency noise formed in the transconductance amplifier such that the noise will not affect the frequencies of interest in the analog sensor input signal.

The Nyquist rate is twice the highest frequency of interest of the analog sensor input signal that is sampled.

The chopping frequency can be freely selected between the Nyquist rate and the sample rate of the delta sigma modulator. The higher the chopping frequency, the better noise reduction may be achieved. However, chopping at high frequency may require higher power consumption, so there is a trade-off between noise reduction and power consumption.

Further, sampling of the analog input sensor signal by the delta sigma modulator at a rate below the chopping frequency may cause folding of noise into baseband such that the chopping frequency may advantageously be lower than the sample rate of the delta sigma modulator.

The first, second, and third chopper may operate at the same chopping frequency such that the upmodulated analog sensor input signal may be recovered by downmodulation by the second and third choppers.

According to an embodiment, the input stage comprises a fourth chopper in a load of an output branch of the input stage.

The fourth chopper allows flicker noise of a current source in the output branch to be upmodulated such that the flicker noise will not affect an output signal at the output branch of the input stage in the bandwidth of frequencies of interest. This may further improve noise performance of the sensor readout circuitry, but it should be realized that the fourth chopper is optional.

According to an embodiment, the transconductance amplifier further comprises a bootstrapping circuitry, wherein the bootstrapping circuitry comprises a bootstrap transistor having a drain current controlled by a bootstrap current source, the bootstrap transistor further comprising a gate connected to a source of the input transistor and a source connected to a drain of the input transistor for reducing effect of gate-drain parasitic capacitance of the input transistor, wherein the bootstrap transistor and the bootstrap current source form part of the flipped voltage follower.

Chopper stabilization may cause degradation of the input impedance of the delta-sigma modulator. This implies that the input impedance of the sensor readout circuitry may be affected by the chopping loop of the sensor readout circuitry. However, thanks to the use of the bootstrapping circuitry, the input impedance of the sensor readout circuitry may be increased.

Since the sensor readout circuitry may provide a high input impedance, the sensor readout circuitry may support readout of analog signals having high impedance without degrading the signal amplitude. Thus, the sensor readout circuitry may be especially suited for use with small electrodes for acquiring the analog sensor input signal, since small electrodes may be associated with a high impedance.

The transconductance amplifier adopting a flipped voltage follower implies that an output resistance at the source of the input transistor is attenuated by a gain of the flipped voltage follower. Therefore, the source of the input transistor may closely follow the gate of the input transistor, since the low output resistance at the source may be sufficient to cope with loading of the source degeneration resistor. Hence, an effect of gate-source parasitic capacitance of the input transistor may be neutralized.

The bootstrap transistor has a drain current which may be fixed by the bootstrap current source. Thus, a source voltage of the bootstrap transistor may follow a gate voltage of the bootstrap transistor. Thanks to the bootstrap transistor having its gate connected to the source of the input transistor and its source connected to the drain of the input transistor, the drain of the input transistor will follow the gate of the input transistor. This implies that an effect of gate-drain parasitic capacitance of the input transistor may also be neutralized.

Since the bootstrap transistor and the bootstrap current source form part of the flipped voltage follower, boosting of input impedance may be achieved within the flipped voltage follower without need of any additional power consumption for input impedance boosting.

According to an embodiment, the bootstrapping circuitry further comprises a cascode transistor having a drain connected to the bootstrap current source, a gate connected to a fixed bias voltage and a source connected to the drain of the bootstrap transistor, wherein the cascode transistor forms part of the flipped voltage follower.

Thus, a cascode transistor may be arranged between the bootstrap transistor and the bootstrap current source. The cascode transistor may have a fixed drain current by being connected to the bootstrap current source and has a fixed gate voltage. The cascode transistor may thus provide attenuation of a signal at the source of the cascode transistor compared to a signal at the drain of the cascode transistor.

Thanks to the attenuation effect of the cascode transistor, a signal swing at a node connected to the drain of the bootstrap transistor compared to at the drain of the cascode transistor is relatively low. This facilitates maintaining the bootstrap transistor in saturation region such that it may be easily ensured that the source voltage of the bootstrap transistor closely follows the gate voltage of the bootstrap transistor.

Further, thanks to the cascode transistor, a current through the bootstrap transistor may be more constant, such that the gate-source voltage of the bootstrap transistor is more constant facilitating that an effect of gate-drain parasitic capacitance of the input transistor is neutralized.

It should be realized that the cascode transistor may be dispensed with in the bootstrapping circuitry, while the bootstrap transistor may be sized accordingly. For instance, by having a longer channel length of the bootstrap transistor and optimizing an aspect ratio, the bootstrap transistor may be maintained to operate in saturation region. However, the use of the cascode transistor may imply that the size of the bootstrap transistor may be reduced such that the sensor readout circuitry may be more compact.

Since the cascode transistor forms part of the flipped voltage follower, the cascode transistor is re-used by forming part of both the flipped voltage follower and the bootstrapping circuitry.

According to an embodiment, the bootstrapping circuitry is arranged within the chopping loop.

Hence, thanks to the bootstrapping circuitry being arranged within the chopping loop formed by the first, second, and third choppers, the flicker noise from the bootstrap transistor and the bootstrap current source may be filtered out so as to improve noise performance of the sensor readout circuitry. Also, if the cascode transistor is used, the flicker noise from this cascode transistor may be filtered out.

Thanks to the chopper stabilization, size of the transistor(s) of the bootstrapping circuitry may be reduced without a risk that the flicker noise affects the readout of the analog sensor input signal. Hence, an area of transistor(s) of the bootstrapping circuitry of the sensor readout circuitry may be small, such that the sensor readout circuitry may be provided in a small area.

According to an embodiment, a bulk gate of the input transistor is connected to a source of the input transistor.

This implies that the bulk gate of the input transistor may follow the source of the input transistor. Hence, an effect of gate-body parasitic capacitance of the input transistor may also be neutralized. Also, this provides further boosting of the input impedance of the delta-sigma modulator.

According to a second aspect, there is provided a biopotential signal sensor, comprising: the sensor readout circuitry according to the first aspect, and at least one electrode configured for sensing a biopotential, wherein the at least one electrode is connected to the pair of input transistors of the sensor readout circuitry.

Effects and features of this second aspect are largely analogous to those described above in connection with the first aspect. Embodiments mentioned in relation to the first aspect are largely compatible with the second aspect.

When detecting biopotential signals, electrode(s) are worn by or implanted in a subject, and at least the sensor readout circuitry receiving electrode signals may also need to be worn by or implanted in the subject. Small size electrodes may be advantageously used, so as to facilitate having a small-size biopotential signal sensor which is to be worn or implanted. When the electrodes are worn by the subject, acquisition of signals from a subject wearing the biopotential signal sensor may be achieved while avoiding or reducing inconvenience to the subject. When electrodes are implanted in the subject, the biopotential signal sensor may be provided with a low invasiveness on the subject.

Small size electrodes may also be used in order to enable sensing distribution of biopotential within a body with a high resolution.

Since the sensor readout circuitry may provide a high input impedance, the sensor readout circuitry may support readout of analog signals having high impedance without degrading the signal amplitude. Thus, the sensor readout circuitry may be especially suited for use with small size electrodes.

Further, the sensor readout circuitry using chopper stabilization may facilitate use of small size transistors while reducing a risk that flicker noise affects the readout of the analog sensor input signal. Hence, the sensor readout circuitry may be small, which further facilitates have a small size biopotential signal sensor to reduce inconvenience to a subject wearing the sensor.

The biopotential signal sensor may comprise a first and a second electrode, wherein the first electrode is configured to sense the biopotential and the second electrode is connected to a reference potential. The first and the second electrodes may then each be connected to a respective one of the input transistors in the pair of input transistors of the sensor readout circuitry.

According to another embodiment, the biopotential signal sensor may comprise one electrode, which is configured to sense the biopotential. This electrode may then be connected to one of the input transistors in the pair of input transistors of the sensor readout circuitry, whereas the other of the input transistors may be directly connected to a reference potential.

It should further be realized that the biopotential signal sensor may comprise an array of sensor readout circuitries for reading out signals from a plurality of electrodes.

The biopotential signal sensor may for instance be configured to sense a biopotential signal relating to electrocardiography, electroencephalography, electrocorticography, or electromyography. However, as further discussed below, the biopotential signal sensor may be of particular interest in a neural probe for sensing potentials in a brain, such as local field potential and action potential.

According to an embodiment, the sensor readout circuitry is arranged on a common substrate with the at least one electrode.

This implies that the biopotential signal sensor may be compact. Further, it may ensure high signal integrity of the electrode signals received by the sensor readout circuitry.

According to a third aspect, there is provided a neural probe, comprising: the biopotential signal sensor according to the second aspect, wherein the at least one electrode is arranged on a carrier configured for being inserted into the brain.

Effects and features of this third aspect are largely analogous to those described above in connection with the first and second aspects. Embodiments mentioned in relation to the first and second aspects are largely compatible with the third aspect.

In neural probes, there is a desire to provide as small electrodes as possible in order to have a high spatial resolution of signals acquired from a brain. Since electrodes are small, the electrodes have high impedance. Therefore, a high input impedance of the sensor readout circuitry is desired so as not to degrade signal quality of the electrode signals. Hence, the sensor readout circuitry is well-suited for use in a neural probe, since the input circuitry may maintain a high input impedance even though noise suppression by a chopping loop is used.

According to a fourth aspect, there is provided a method for readout of an analog sensor input signal; said method comprising: receiving the analog sensor input signal at an input stage of a delta-sigma modulator; chopping the analog sensor input signal by a first chopper before the analog sensor input signal is received at a gate of an input transistor of a transconductance amplifier of the input stage; chopping a signal between input transistor and a source degeneration resistor by a second chopper such that a baseband signal is provided at a node of the source degeneration resistor; following the analog sensor input signal by a flipped voltage follower of the transconductance amplifier and a current mirror such that a voltage across a source degeneration resistor follows the analog sensor input signal, wherein a signal in the flipped voltage follower is chopped by a third chopper before a connection to shared gates of the current mirror such that signals in the current mirror are in baseband; receiving a feedback signal from a digital-to-analog converter of the delta-sigma modulator at the node of the source degeneration resistor; subtracting the feedback signal from the analog sensor input signal by the transconductance amplifier and outputting a corresponding mirrored signal by the current mirror for quantizing of the analog sensor input signal by the delta-sigma modulator; outputting a read out digital signal by the delta-sigma modulator.

Effects and features of this fourth aspect are largely analogous to those described above in connection with the first, second, and third aspects. Embodiments mentioned in relation to the first, second, and third aspects are largely compatible with the fourth aspect.

Thanks to the method, chopper stabilization may be utilized while the feedback signal from the DAC is received at the node of the source degeneration resistor, wherein a baseband signal of the analog sensor input signal is provided. This implies that any quantization noise is not folded due to chopping such that folding of quantization noise into signal band may be avoided.

Further, thanks to the input transistor being arranged between the first and second choppers, the flicker noise from the input transistor may be filtered out so as to improve noise performance of the method of reading out the analog sensor input signal.

According to an embodiment, the method further comprises boosting input impedance of the input transistor of the transconductance amplifier by a bootstrapping circuitry.

Chopper stabilization may cause degradation of the input impedance of the delta-sigma modulator. This implies that the input impedance may be affected by the chopping of the analog sensor input signal. However, thanks to the use of the bootstrapping circuitry, the input impedance may be increased, such that degradation of a signal amplitude in readout of the analog sensor input signal may be avoided. Thus, the method may be especially suited for use with small electrodes for acquiring the analog sensor input signal, since small electrodes may be associated with a high impedance.

BRIEF DESCRIPTION OF THE DRAWINGS

The above, as well as additional objects, features and advantages of the present inventive concept, will be better understood through the following illustrative and non-limiting detailed description, with reference to the appended drawings. In the drawings like reference numerals will be used for like elements unless stated otherwise.

DETAILED DESCRIPTION

Figure 1:
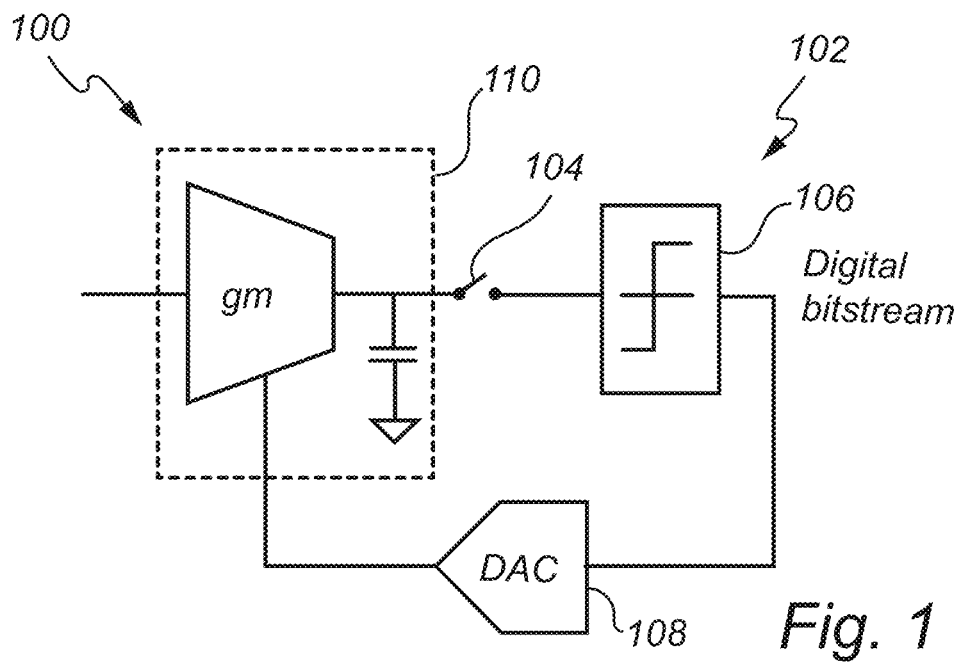
FIG. 1 is a schematic view of a sensor readout circuitry including a delta-sigma modulator according to an embodiment.

Referring now to FIG. 1, a sensor readout circuitry 100 according to an embodiment will be described. The sensor readout circuitry 100 is configured to receive an input signal from an analog sensor, herein called an analog sensor input signal, and to convert the analog sensor input signal to a digital signal.

As shown in FIG. 1, the sensor readout circuitry 100 may comprise a delta-sigma modulator 102, which receives the analog sensor input signal and outputs a digital signal so as to perform analog-to-digital conversion of the analog sensor input signal.

Delta-sigma modulators 102 are known by the person skilled in the art, and the delta-sigma modulator 102 will therefore be only briefly discussed below. Then, an input stage 110 of the delta-sigma modulator 102 will be described in detail, such that the initial description of the delta-sigma modulator 102 describes a context in which the input stage 110 is provided.

The delta-sigma modulator 102 comprises the input stage 110, which may act as a loop filter of the delta-sigma modulator 102 and further may perform subtraction of a feedback signal from the analog sensor input signal.

As will be described in further detail below, the input stage 110 comprises a transconductance amplifier, which may ensure that the sensor readout circuitry 100 provides a high input impedance.

The delta-sigma modulator 102 may further comprise a sampling stage 104 for sampling the analog sensor input signal. As shown in FIG. 1, the sampling stage 104 may be arranged after the input stage 110 such that the analog sensor input signal passes the loop filter of the input stage 110 before being sampled. Thus, the delta-sigma modulator 102 may form a continuous-time delta-sigma modulator (CTDSM), wherein the loop filter acts as an anti-aliasing filter.

The delta-sigma modulator 102 may further comprise a quantizer 106 for forming a digital code based on the analog sensor input signal. In case the quantizer 106 is a single-bit quantizer, a digital bitstream will be produced. The digital code or bitstream may be further processed by a decimation filter (not shown) for forming a digital representation of the analog sensor input signal.

The signal from the quantizer 106 is also passed through a digital-to-analog converter (DAC) 108 for providing a feedback signal in analog domain to the input stage 110. The input stage 110 subtracts the feedback signal from the analog sensor input signal. A resulting signal, being a difference between the analog sensor input signal and the feedback signal, may then be integrated in the delta-sigma modulator 102.

Figure 2:
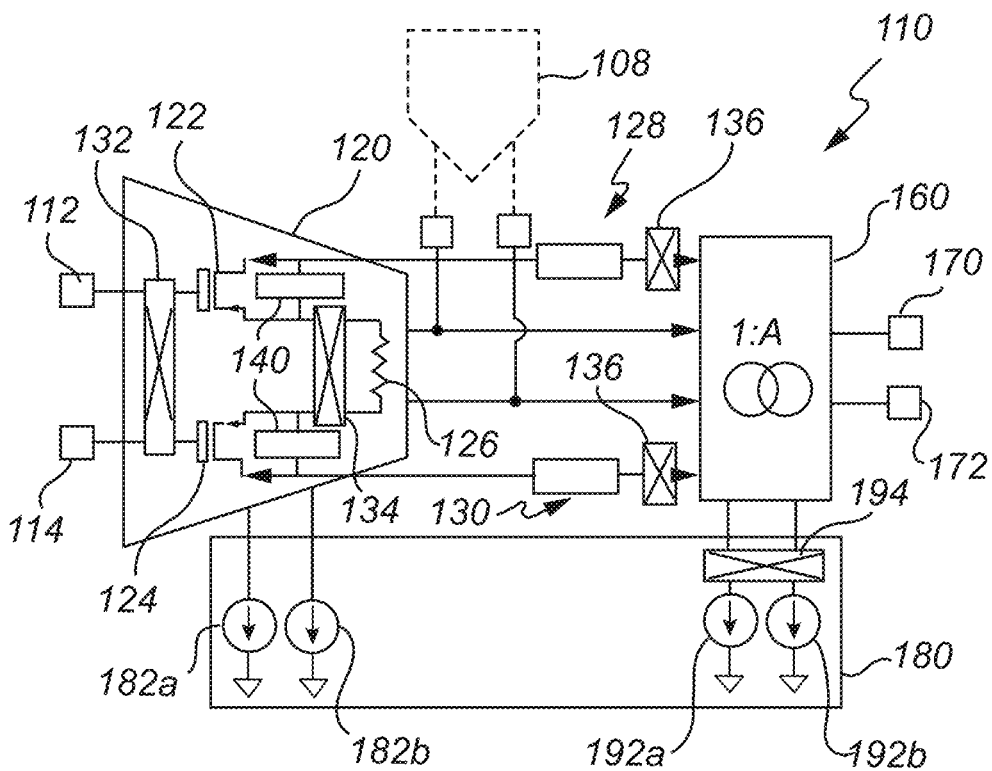
FIG. 2 is a schematic view of an input stage of the delta-sigma modulator according to an embodiment.

Referring now to FIG. 2, the input stage 110 of the delta-sigma modulator 102 according to an embodiment will be further described.

The input stage 110 comprises a transconductance amplifier having a transconductance part 120, a current mirror part 160, and current sources 180.

The sensor readout circuitry 100 comprises a first and a second input terminal 112, 114. The sensor readout circuitry 100 may receive an analog sensor input signal on the first input terminal 112 and a reference input signal on the second input terminal 114. For instance, the sensor readout circuitry 100 may be connected to an electrode for receiving the analog sensor input signal and may be connected to a reference electrode or directly to a reference potential for receiving the reference input signal.

The transconductance part 120 comprises a pair of input transistors 122, 124. Each of the input transistors 122, 124 in the pair may be associated with a respective one of the first input terminal 112 and the second input terminal 114.

The input transistors 122, 124 are indicated in FIG. 2 as being p-type metal-oxide-semiconductor (PMOS) transistors. However, it should be realized that n-type metal-oxide-semiconductor (NMOS) transistors may be used instead. Below, description is made in relation to the input transistors 122, 124 being PMOS transistors. It should be realized that if NMOS transistors are used instead, all transistors in the below description should also change type from PMOS to NMOS or vice versa.

The transconductance part 120 further comprises a source degeneration resistor 126 and voltage potentials at nodes on each side of the source degeneration resistor 126 are configured to follow the signals received by the pair of input transistors 122, 124.

The input stage 110 is configured to receive the feedback signal from the DAC 108 (indicated in dashed lines in FIG. 2) at the nodes on each side of the source degeneration resistor 126. The feedback signal is subtracted from the signal across the source degeneration resistor 126 in the transconductance part 120 and a resulting signal from the subtraction is mirrored by the current mirror part 160 to first and second output terminals 170, 172 of the current mirror part 160.

The transconductance part 120 and the current mirror part 160 incorporate a first and a second flipped voltage follower 128, 130, wherein the first flipped voltage follower 128 is arranged between the first input terminal 112 and a first node on one side of the source degeneration resistor 126 and the second flipped voltage follower 130 is arranged between the second input terminal 114 and a second node on an opposite side of the source degeneration resistor 126 to the first node. Thus, the voltage across the source degeneration resistor 126 may follow closely the input signals on the input terminals 112, 114.

Chopper stabilization is used in the transconductance part 120 such that impact of flicker noise from components of the input stage 110 may be reduced. A chopping loop is formed, wherein the input transistors 122, 124 and the current sources 180 are arranged within the chopping loop such that flicker noise from the input transistors 122, 124 and the current sources 180 is reduced.

The nodes on opposite sides of the source degeneration resistor 126 are outside the chopping loop, such that the input signals received on the input terminals 112, 114 is brought back to baseband at the nodes in which the feedback signal is received. This implies that any high frequency noise in the feedback signal is not folded by the chopping loop into baseband so that such high frequency noise will not affect readout of the analog sensor input signal.

The transconductance part 120 comprises a first chopper 132 between the input terminals 112, 114 and the input transistors 122, 124 for upmodulating the signals received on the input terminals 112, 114.

The transconductance part 120 further comprises a second chopper 134 between the input transistors 122, 124 and the nodes on opposite sides of the source degeneration resistor 126, at which the feedback signal is received. Hence, the second chopper 134 is configured to downmodulate the signals received on the input terminals 112, 114 back to baseband at the nodes in which the feedback signal is received.

The transconductance part 120 further comprises a third chopper 136 between the transconductance part 120 and the current mirror part 160 before a connection of the transconductance part 120 to shared gates of the current mirror part 160. This implies that the signals in the current mirror part 160 are also in baseband.

The current mirror part 160 may be connected in the first and second flipped voltage followers 128, 130 to the nodes in which the feedback signal is received. The flipped voltage followers 128, 130 may contribute to low output impedance for current flowing into the current mirror part 160. Thus, a feedback current may flow into the current mirror part 160 so as to avoid that the feedback current is chopped by the second chopper 134. Further, since the signals in the current mirror part 160 are also in baseband, by downmodulation by the third chopper 136, there is no folding of noise from the feedback current in the current mirror part 160.

The chopping loop is formed between the first chopper 132 and the second chopper 134 and the third chopper 136.

The chopper stabilization used in the input stage 110 implies that an input impedance of the sensor readout circuitry 100 is reduced. In order to increase input impedance of the sensor readout circuitry 100, the transconductance part 120 further comprises a bootstrapping circuitry 140 connected to the input transistors 122, 124.

Thus, the input stage 110 provides the sensor readout circuitry 100 with a high input impedance while also using chopper stabilization for reducing impact of flicker noise on readout of input signals.

The input stage 110 may further comprise integrating capacitors connected to the first and second output terminals 170, 172 of the current mirror part 160. Thus, the integrating capacitors may be configured to integrate the resulting signal from subtracting the feedback signal from the analog sensor input signal.

Figure 3:
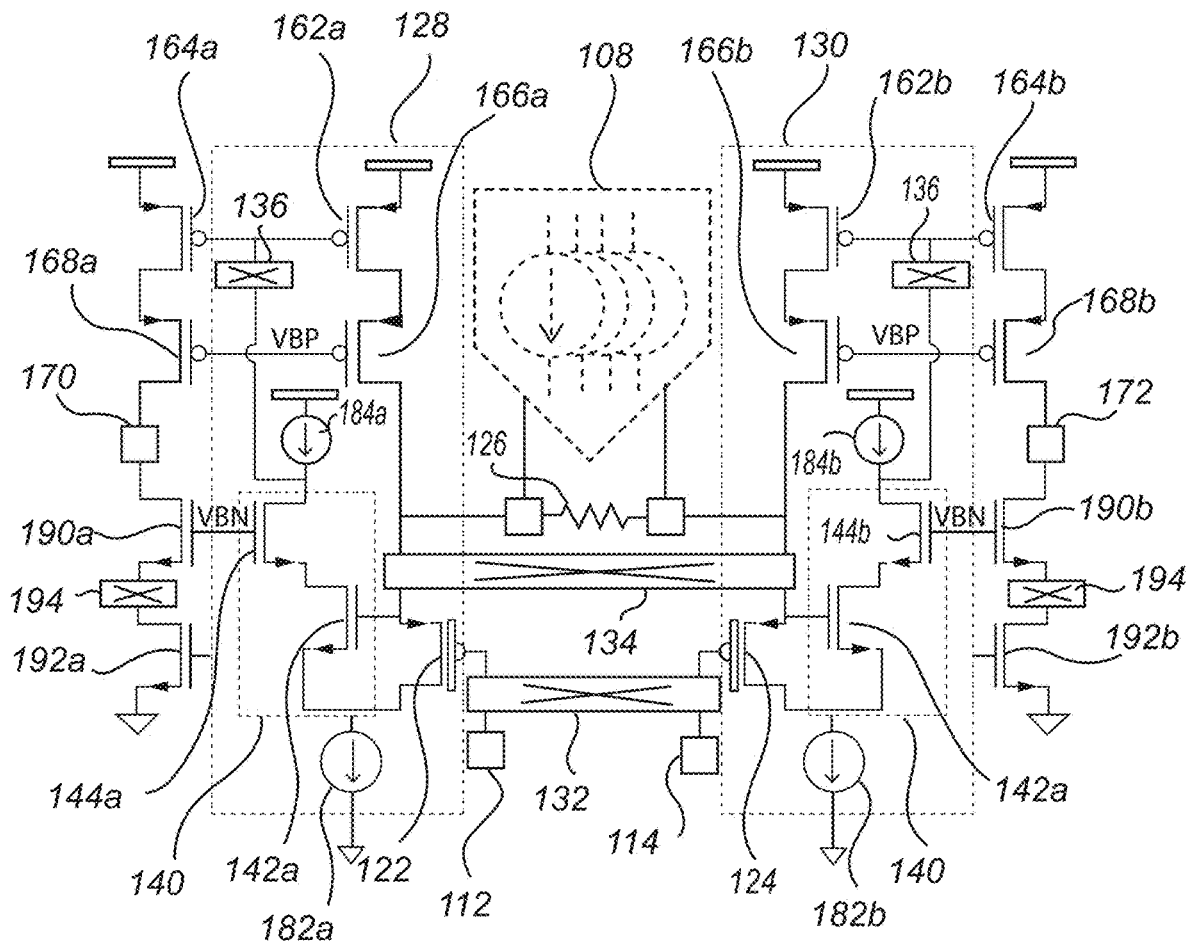
FIG. 3 is a wiring diagram of the input stage of FIG. 2.

Referring now to FIG. 3, the input stage 110 will be described in further detail. In FIG. 3, components of the transconductance part 120, the current mirror 160 and the current sources 180 are illustrated in a wiring diagram, such that borders of the respective parts are not clearly outlined in FIG. 3. Rather, the below description will make clear to which part each of the components belong.

The current mirror part 160 may comprise a first and a second portion, each associated with processing the signal at a respective side of the source degeneration resistor 126. Each of the portions of the current mirror part may comprise two pairs of transistors, indicated as transistors 162a, 164a, 166a, and 168a for the first portion of the current mirror part 160 and corresponding transistors 162b, 164b, 166b and 168b for the second portion of the current mirror part 160. Below, discussion is made only in relation to the first portion of the current mirror part 160. However, it should be understood that the second portion of the current mirror part 160 may be arranged in the same manner. The transistors 162a, 164a, 166a, 168a and 162b, 164b, 166b, 168b are shown in FIG. 3 as being PMOS transistors. However, it should be realized that NMOS transistors may be used instead, if the input transistors 122, 124 are NMOS transistors.

The transistors 162a, 164a form a first pair of the current mirror part 160 with gates of the transistors 162a, 164a connected to each other. Further, the transistors 166a, 168a form a second pair of the current mirror part 160 with gates of the transistors 166a, 168a connected to each other.

The gates of the transistors 166a, 168a may be provided with a fixed positive bias voltage, VBP. The gates of the transistors 162a, 164a may be connected to the third chopper 134 forming part of the first flipped voltage follower 128.

The transistor 162a may have a source connected to a ground voltage and a drain connected to a source of the transistor 166a. Thus, the transistors 162a, 166a may be arranged as cascode transistors. The transistor 166a may further have a drain connected to the first node on one side of the source degeneration resistor 126.

The transistor 164a may have a source connected to a ground voltage and a drain connected to a source of the transistor 168a. Thus, the transistors 162a, 166a may be arranged as cascode transistors. The transistor 168a may further have a drain connected to the first output terminal 170.

The current mirror part 160 is configured such that a current flowing from the first node on one side of the source degeneration resistor 126 through the transistors 166a, 162a is mirrored through the transistors 164a, 168a to the first output terminal 170.

It should be realized that the current mirror part 160 may be implemented in other manners as would be readily understood by the person skilled in the art. For example, the transistors 166a, 168a, 166b, 168b are optional and need not be included in the current mirror part 160.

The input stage 110 further comprises a first and a second flipped voltage follower 128, 130, indicated by dashed lines in FIG. 3. Below, discussion is made mainly in relation to the first flipped voltage follower 128. However, it should be understood that the second flipped voltage follower 130 may be arranged in the same manner.

The transconductance part 120 and the current mirror part 160 incorporate the first flipped voltage follower 128. The first flipped voltage follower 128 comprises a first input transistor 122 of the pair of input transistors 122, 124 of the transconductance part 120. The first flipped voltage follower 128 is configured to receive an input signal on a gate of the first input transistor 122 and to provide an output signal at the first node on one side of the source degeneration resistor 126. The first node is connected to a source of the first input transistor 122.

The first flipped voltage follower 128 may further comprise the transistors 162a, 166a of the current mirror part 160. The gate of the transistor 162a may further be connected to a drain of the first input transistor 122 via the bootstrapping circuitry 140 of the transconductance part 120, indicated by dashed lines in FIG. 3. The drain of the first input transistor 122 is further connected to a first current source 182a providing a fixed drain current of the first input transistor 122.

As shown in FIG. 3, the bootstrapping circuitry 140 comprises a first bootstrap transistor 142a and, optionally, a first cascode transistor 144a. The first bootstrap transistor 142a or the first cascode transistor 144a, if the bootstrapping circuitry 140 comprises the first cascode transistor 144a, may have a drain connected to a first bootstrap current source 184a for providing a fixed drain current. The bootstrapping circuitry 140 will be described in further detail below.

The first bootstrap transistor 142a, the first cascode transistor 144a, and the first bootstrap current source 184a may form part of the first flipped voltage follower 128 such that bootstrapping may be provided within components of the first flipped voltage follower 128. The bootstrapping circuitry 140 also boosts a gain of the feedback loop in the flipped voltage followers 128, 130 such that equivalent resistance on nodes on opposite sides of the source degeneration resistor 126 is reduced.

Similar to the description above of the first flipped voltage follower 128, the second flipped voltage follower 130 may comprise a second bootstrap transistor 142b, optionally a second cascode transistor 144b and a second bootstrap current source 184b forming a bootstrapping circuitry 140 within the second flipped voltage follower 130. Further, a drain of the second input transistor 124 is further connected to a second current source 182b providing a fixed drain current of the second input transistor 124.

As already discussed above in relation to FIG. 2, FIG. 3 also shows the first chopper 132 between the input terminals 112, 114 and the gates of the input transistors 122, 124. Also, the second chopper 134 is arranged between the sources of the input transistors 122, 124 and the nodes on opposite sides of the source degeneration resistor 126. Further, the third chopper 136 is arranged between the gates of the transistors 162a, 162b of the current mirror part 160 and the bootstrapping circuitry 140 in the flipped voltage followers 128, 130.

A chopping loop is formed between the first chopper 132 and the second and third choppers 134, 136, wherein the input transistors 122, 124 and the current sources 182a, 182b, 184a, 184b are arranged within the chopping loop such that flicker noise from the input transistors 122, 124 and the current sources 182a, 182b, 184a, 184b is reduced.

FIG. 3 also shows two portions of a load of an output branch of the input stage 110, each portion being associated with a respective one of the output terminals 170, 172. Below, discussion is made only in relation to a first portion of the load of the output branch associated with the first output terminal 170, wherein the first portion comprises a first transistor 190a, and a current source 192a. However, it should be understood that the second portion of the load of the output branch associated with the second output terminal 172 may be arranged in the same manner, illustrated by transistor 190b and current source 192b in FIG. 3.

Thus, the load may comprise a first transistor 190*a*, shown in FIG. 3 as an NMOS transistor, having a drain connected to the first output terminal 170 and being configured to receive a fixed gate voltage VBN on a gate. The first transistor 190*a* may further have a source connected to a current source 192*a*, which is shown in FIG. 3 as an NMOS transistor being arranged to receive a common-mode feedback voltage on a gate for controlling the current in the transistor to stabilize the common-mode voltage at the output terminal 170.

The input stage 110 may further comprise a fourth chopper 194 between the first transistor 190*a* and the current source 192*a*. The fourth chopper 194 allows the signal in the output branch to be upmodulated such that flicker noise of a current source 192*a* in the output branch will not affect an output signal at the output branch of the input stage 110. This may further improve noise performance of the sensor readout circuitry 100, but it should be realized that the fourth chopper 194 is optional.

Figure 4:
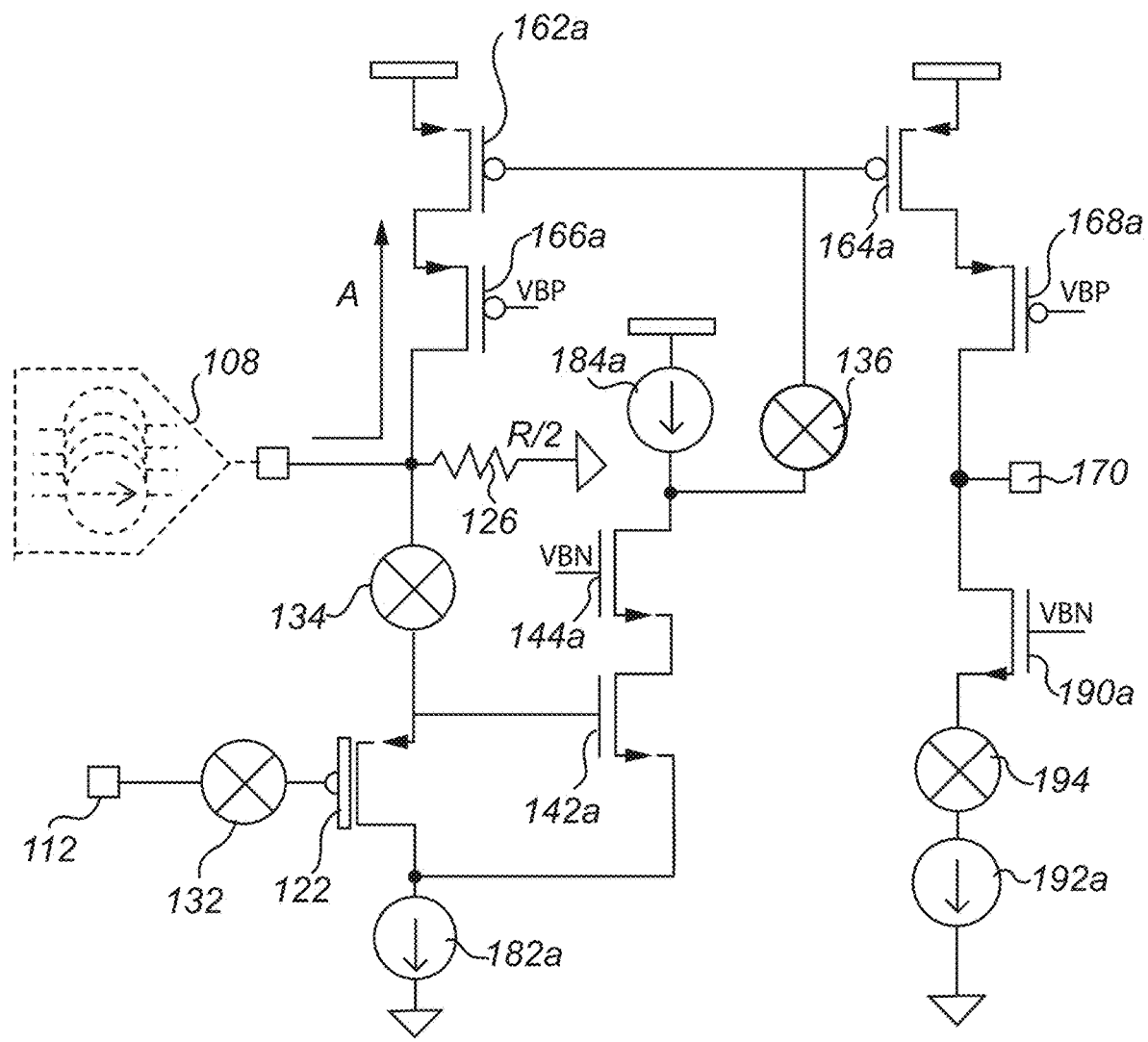
FIG. 4 is a wiring diagram illustrating a chopping loop and a flipped voltage follower of the input stage.

Referring now to FIG. 4, the chopping loop formed by the choppers will now be described in further detail. FIG. 4 illustrates the sensor readout circuitry 100 in relation to only one side of the circuitry between the first input terminal 112 and the first output terminal 170, and it should be realized that the other side of the circuitry between the second input terminal 114 and the second output terminal 172 may be arranged in the same manner.

The chopping loop may be defined by four choppers.

The first chopper 132 is placed at the input, between the input terminal 112 and the input transistor 122, and the first chopper 132 upmodulates the input signal.

The second chopper 134 is placed between the input transistor 122 and the source degeneration resistor 126 and thus the signals at the node of the source degeneration resistor 126 at which DAC feedback is received are in the baseband.

The third chopper 136 is placed before the connection to the shared gates of the current mirror part 160 and thus the signals in the current mirror part 160 are also in the baseband.

The fourth chopper 194, which is optional, is placed in the load of the output branch.

As shown in FIG. 4, components within the chopping loop include the input transistor 122, the transistors 142*a*, 144*a* used for bootstrapping and the current sources 182*a*, 184*a*, 192*a* which are dominant contributors to flicker noise if chopping is not applied. With this chopping scheme, the contribution of these components to flicker noise is effectively eliminated.

The first chopper 132 is configured to upmodulate the analog sensor input signal such that a bandwidth of frequencies of interest in the analog sensor input signal are within the chopping frequency of the first chopper 132. This implies that the frequencies of interest will be upmodulated by the first chopper 132. The frequencies of interest may again be downmodulated to baseband by the second chopper 134, while the modulation by the second chopper 134 may upmodulate low frequency noise formed in the transconductance part 120 such that the noise will not affect the frequencies of interest in the analog sensor input signal.

The first, second, and third choppers 132, 134, 136 may operate at the same chopping frequency such that the upmodulated analog sensor input signal may be recovered by downmodulation by the second and third choppers 134, 136.

Thanks to the flipped voltage follower 128 contributing to a low output impedance in a direction of the current mirror part 160, the feedback current from the DAC 108, as indicated by arrow A, will flow into the current mirror part 160 which is outside the chopping loop. In this way, folding of high-frequency-shaped quantization noise into baseband is avoided.

Figure 5:
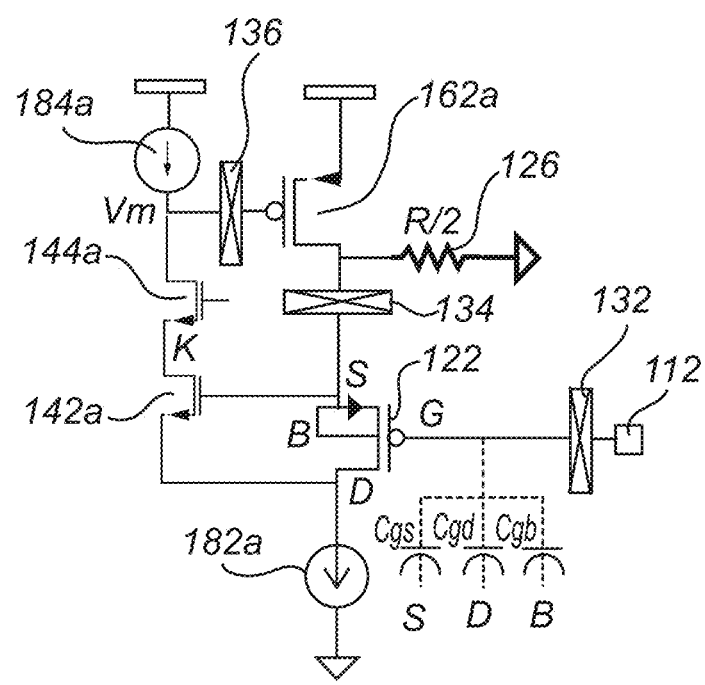
FIG. 5 is a wiring diagram illustrating a bootstrapping circuitry of the input stage.

Referring now to FIG. 5, the bootstrapping circuitry 140 will be further described. FIG. 5 illustrates the bootstrapping circuitry 140 in relation to only the first flipped voltage follower 128 at one side of the sensor readout circuitry 100, and it should be realized that the bootstrapping circuitry 140 in relation to the second flipped voltage follower 130 may be arranged in the same manner. For simplification, FIG. 5 only shows one of the cascode transistors 162*a* of the current mirror part 160.

The bootstrapping circuitry 140 comprises the first bootstrap transistor 142*a* having a drain current controlled by the first bootstrap current source 184*a*. This may be achieved by a drain of the first bootstrap transistor 142*a* being connected to the first bootstrap current source 184*a* or alternatively via the first cascode transistor 144*a* having a drain connected to the first bootstrap current source 184*a* and a source connected to the drain of the first bootstrap transistor 142*a*.

The first bootstrap transistor 142*a* has a gate connected to the source of the input transistor 122. Further, the first bootstrap transistor 142*a* has a source connected to the drain of the input transistor 122. The drain current of the input transistor is fixed by the current source 182*a* and, thus, the source voltage (node S in FIG. 5) of the input transistor 122 will follow the gate voltage (node G in FIG. 5) of the input transistor 122. In this way the drain (node D in FIG. 5) of the input transistor 122 will follow the gate of the input transistor 122 and thus neutralize an effect of a gate-drain parasitic capacitance, illustrated by capacitor Cgd in FIG. 5.

Since the input stage 110 uses a flipped voltage follower feedback loop, an output resistance at node S is attenuated by a loop gain of the flipped voltage follower 128. Therefore, the signal at node S will follow closely the signal at node G since the low output resistance at node S is sufficient to cope with a loading of the source degeneration resistor 126. In this way, an effect of a gate-source parasitic capacitance, illustrated by capacitor Cgs in FIG. 5, is neutralized.

A bulk gate (node B in FIG. 5) of the input transistor 122 may be connected to the source of the input transistor 122. This implies that an effect of a gate-body parasitic capacitance, illustrated by capacitor Cgb in FIG. 5, is neutralized.

The first cascode transistor 144*a* has a fixed drain current defined by the first bootstrap current source 184*a* and is further configured to receive a fixed gate voltage VBN. Thus, the signal at the source (node K in FIG. 5) of the first cascode transistor 144*a* will be much attenuated by approximately an intrinsic gain of the first cascode transistor 144*a* compared with the signal at the drain (node Vm in FIG. 5) of the first cascode transistor 144*a*. The intrinsic gain of the first cascode transistor 144*a* may be given by gm*rds, where gm is a transconductance of the first cascode transistor 144*a* and rds is a resistance between drain and source of the first cascode transistor 144*a* during operation.

The node Vm modulates the transistor 162*a* of the current mirror part 160 to supply a current that flows into the source degeneration resistor 126 and thus the node Vm will have relatively large signal swing. With the attenuation effect of the first cascode transistor 144*a*, the signal swing at node K will be trivial. Hence, the first cascode transistor 144*a* facilitates keeping the first bootstrap transistor 142*a* in saturation region. Further, a short-channel effect of the first bootstrap transistor 142*a* will be negligible and thus the source voltage of the first bootstrap transistor 142*a* will follow closely the gate voltage of the first bootstrap transistor 142*a*.

It should be realized that the use of the first cascode transistor 144*a* is optional as a function of the first cascode transistor 144*a* can be substituted by sizing the first bootstrap transistor 142*a* accordingly. For instance, the first bootstrap transistor 142*a* may be provided with a longer channel length and/or an aspect ratio of the first bootstrap transistor 142*a* may be optimized to maintain saturation operation of the first bootstrap transistor 142*a* across process-voltage-temperature (PVT) variations.

The input transistor 122 may be provided with a large gate oxide thickness. This implies that a gate leakage current at node G is small.

An equivalent input impedance $Z_{in}$ at the input terminal 112 of the sensor readout circuitry 100 using the chopping loop is given by:

$$Zin \approx \frac{1}{4 C_G f_{CHOP}}$$

where $C_G$ is a total equivalent capacitance at node G and $f_{CHOP}$ is the chopping frequency of the first chopper 132. A contribution of parasitic capacitances of the input transistors 122, 124 is neutralized for each parasitic capacitance as mentioned above, since signals at nodes G, S, B, and D follow each other closely. Therefore, the input impedance is significantly boosted.

The bootstrapping circuitry 140 does not affect power consumption of the sensor readout circuitry 100. The first and second bootstrap current sources 184*a*, 184*b* used to bias the first bootstrap transistor 142*a* and first cascode transistor 144*a*, and second bootstrap transistor 142*b* and second cascode transistor 144*b*, respectively, are anyway used for constructing the first and second flipped voltage followers 128, 130.

The bootstrapping circuitry 140 allows a wider input common-mode range. The use of the first bootstrap transistor 142*a* automatically keeps the drain-source voltage of the input transistor 122 equal to its gate-source voltage and thus the input transistor 122 can stay in saturation region even if the input common-mode voltage varies significantly.

Figure 6:
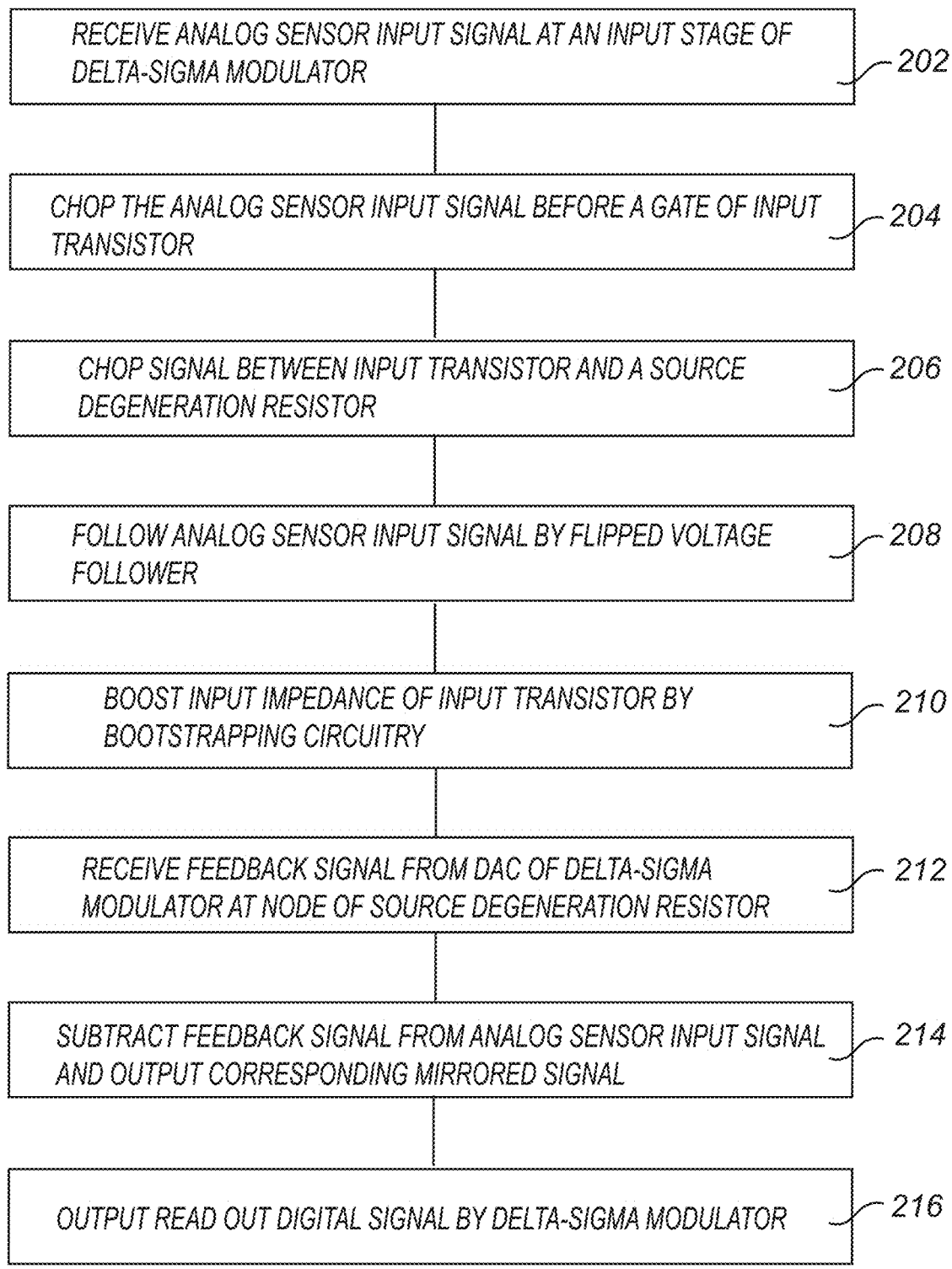
FIG. 6 is a flowchart of a method according to an embodiment.

Referring now to FIG. 6, a method according to an embodiment will be described.

The method may comprise receiving 202 the analog sensor input signal at the input stage 110 of the delta-sigma modulator 102. The analog sensor input signal may be received from an electrode being connected to the first input terminal 112. In addition, the second input terminal may be connected to a reference potential or may receive a reference input signal, e.g. from a reference electrode.

The method may further comprise chopping 204 the analog sensor input signal by the first chopper 132 before the analog sensor input signal is received at the gate of the first input transistor 122 of the transconductance amplifier 120 of the input stage 110.

The method may further comprise chopping 206 a signal between the first input transistor 122 and the source degeneration resistor 126 of the transconductance amplifier 120 by the second chopper 134 such that a baseband signal is provided at a node of the source degeneration resistor 126. Hence, the analog sensor input signal is upmodulated by the first chopper 132 and downmodulated back to baseband by the second chopper 134 such that flicker noise from components between the first and the second chopper 132, 134 will not affect reading out of the analog sensor input signal at the source degeneration resistor 126.

The method may further comprise following 208 the analog sensor input signal by the first flipped voltage follower 128 incorporated in the transconductance amplifier 120 and the current mirror 160 such that a voltage across the source degeneration resistor 126 follows the analog sensor input signal. Further, a signal in the flipped voltage follower 128 is chopped by a third chopper 136 before a connection to shared gates of the current mirror 160 such that signals in the current mirror are in baseband.

The method may further comprise boosting 210 input impedance of the input transistor 122 of the transconductance amplifier 120 by the bootstrapping circuitry 140. The input impedance of the input transistor 122 is degraded due to the chopper stabilization provided by the first, second and third choppers 132, 134, 136. Hence, by boosting the input impedance, a high input impedance may be provided such that the method may support readout of analog signals having high impedance without degrading the signal amplitude.

The method may further comprise receiving 212 the feedback signal from the digital-to-analog converter 108 of the delta-sigma modulator 102 at the node of the source degeneration resistor 126. Thus, the analog sensor input signal is in baseband at the node where the feedback signal is received. Further, the flipped voltage follower 128 contributes to low output impedance for current flowing into the current mirror 160. Thus, the feedback current may flow into the current mirror 160 so as to avoid that the feedback current is chopped by the second chopper 134. Further, since the signals in the current mirror 160 are also in baseband, by downmodulation by the third chopper 136, there is no folding of noise from the feedback current in the current mirror 160. This implies that any high frequency noise in the feedback signal, such as quantization noise will not be folded into baseband and will not affect the readout of the analog sensor input signal.

The method may further comprise subtracting 214 the feedback signal from the analog sensor input signal by the transconductance amplifier 120 and outputting a corresponding mirrored signal by the current mirror 160. Thus, the input stage 110 may perform subtraction of the feedback signal from the input signal for the delta-sigma modulator 102.

The mirrored signal that is outputted may first be integrated in integrating capacitors and may thereafter be quantized by the delta-sigma modulator 102 to form a digital bitstream. The digital bitstream may be provided to the DAC 108 for generating the feedback signal to the input stage 110.

Further, the method may comprise outputting 216 a read out digital signal by the delta-sigma modulator 102. The digital signal that is outputted may be based on the digital bitstream from quantizing by the delta-sigma modulator 102. For instance, the digital bitstream may pass a decimation filter for forming the digital signal that is outputted.

Figure 7:
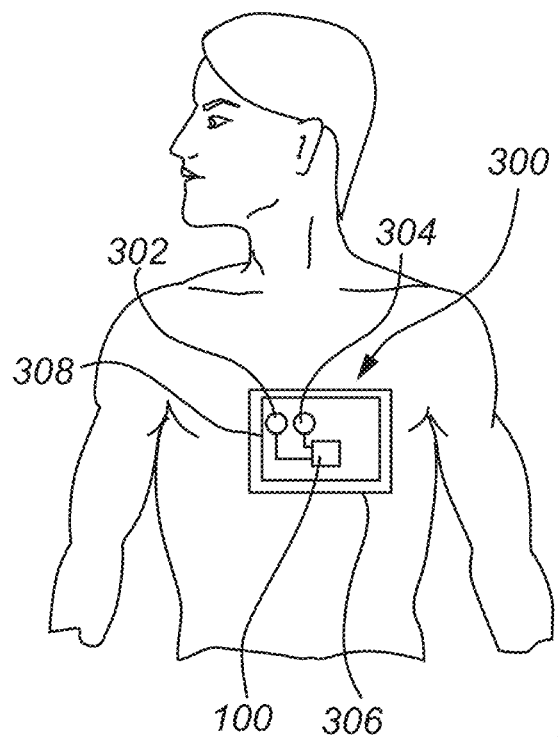
FIG. 7 is a schematic view of a biopotential signal sensor according to an embodiment.

Referring now to FIG. 7, a biopotential signal sensor system 300 according to an embodiment will be described.

The biopotential signal sensor 300 comprises at least one electrode 302 configured for sensing a biopotential signal. The biopotential signal sensor 300 further comprises the sensor readout circuitry 100. The sensor readout circuitry 100 may be configured to receive an analog sensor input signal in the form of a biopotential signal from the at least one electrode 302 and to readout the biopotential signal by the sensor readout circuitry 100 to form a digital representation of the biopotential signal.

The biopotential signal sensor 300 may comprise a first and a second electrode 302, 304, wherein the first electrode 302 is configured to sense the biopotential and the second electrode 304 is connected to a reference potential. The first and the second electrodes 302, 304 may then each be connected to a respective one of the input transistors 122, 124 in the pair of input transistors of the sensor readout circuitry 100.

According to another embodiment, the biopotential signal sensor may comprise one electrode, which is configured to sense the biopotential. This electrode may then be connected to one of the input transistors 122 in the pair of input transistors of the sensor readout circuitry, whereas the other of the input transistors 124 may be directly connected to a reference potential.

It should further be realized that the biopotential signal sensor may comprise an array of sensor readout circuitries 100 for reading out signals from a plurality of electrodes. As a further alternative, the plurality of electrodes may be sequentially connected to the first input terminal 112 of the sensor readout circuitry 100 such that the sensor readout circuitry 100 may support readout of biopotential signals from a plurality of electrodes. The second input terminal 114 may be connected to one reference electrode or a reference potential during the sequence of reading out biopotential signals from the plurality of electrodes, such that the reference electrode/reference potential is shared by the plurality of electrodes.

The at least one electrode 302 may be any type of electrode 302 which is configured to sense an electrical potential at a location of the electrode 302.

The electrode 302 may therefore comprise a conducting part which is configured to sense the electrical potential. The electrode 302 could be adapted to be used for sensing biopotential, i.e. an electrical potential in a body of a human being or an animal.

The biopotential signal sensor 300 may be configured to be worn by a subject. The biopotential signal sensor 300 may thus comprise a carrier configured for attachment to the subject or for arrangement around a body part of the subject. For instance, the biopotential signal sensor 300 may comprise a patch 306 for attaching the biopotential signal sensor system 300 to the subject.

The biopotential signal sensor 300 may comprise further processing circuitry for further processing of the biopotential signals read out by the sensor readout circuitry 100. Thus, the biopotential signal sensor 300 may provide analysis of the biopotential signals.

The biopotential signal sensor 300 may also or alternatively comprise a communication unit for wired or wireless communication to a remote unit for further processing of the biopotential signals. The biopotential signal sensor 300 may communicate the biopotential signals output by the sensor readout circuitry 100 to the remote unit or may further process the biopotential signals before communicating the further processed signals to the remote unit.

The sensor circuitry 100 may be arranged on a common substrate 308 with the at least one electrode 302. This implies that the biopotential signal sensor 300 may be compact. Further, it may ensure high signal integrity of the biopotential signals received by the sensor readout circuitry 100.

The biopotential signal sensor may for instance be configured to sense a biopotential signal relating to electrocardiography, electroencephalography, electrocorticography, or electromyography. However, as further discussed below, the biopotential signal sensor may be of particular interest in a neural probe for sensing potentials in a brain, such as local field potential and action potential.

Figure 8:
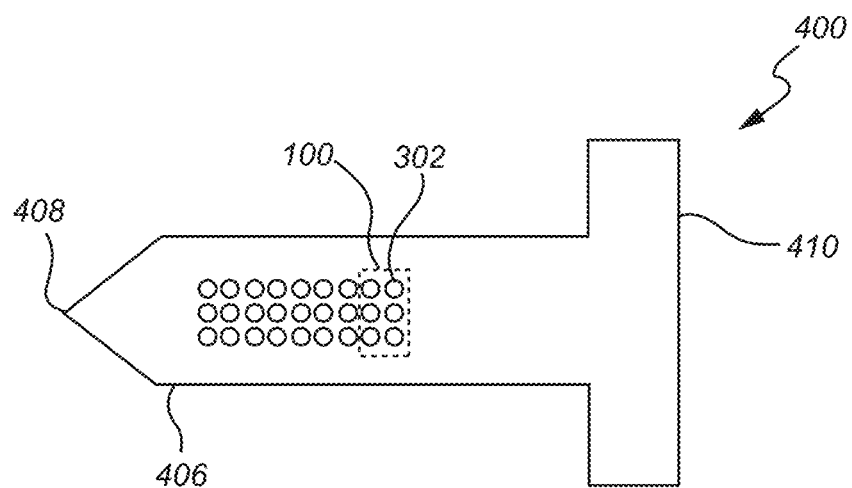
FIG. 8 is a schematic view of a neural probe according to an embodiment.

Referring now to FIG. 8, a neural probe 400 according to an embodiment will be described. The neural probe 400 may incorporate electrodes 302 and the sensor readout circuitry 100 of the biopotential signal sensor 300 as described above.

In the neural probe 400, small electrodes 302 are used in order to have a high spatial resolution of signals acquired from a brain. Since electrodes 302 are small, the electrodes 302 have high impedance. Therefore, a high input impedance of the sensor readout circuitry 100 is desired so as not to degrade signal quality of the electrode signals. Hence, the sensor readout circuitry 100 as described above is well-suited for use in the neural probe 400, since the sensor readout circuitry 100 may maintain a high input impedance while providing chopper stabilization to improve noise performance.

The electrodes 302 may be arranged on a carrier 406 configured for being inserted into the brain to allow the electrodes 302 to acquire signals from the brain. The carrier 406 may have a pointed tip 408 for facilitating insertion into the brain and may have a base portion 410 which is intended not to be inserted into the brain.

The electrodes 302 are arranged in the portion of the carrier 406 intended to be inserted into the brain. The sensor readout circuitry 100 may be arranged in the portion of the carrier 406 intended to be inserted into the brain, such that the sensor readout circuitry 100 may be arranged in a layer below the electrodes 302, illustrated as dashed lines for the sensor readout circuitry 100 supporting the electrodes 302 above the input circuitry 100. As indicated in FIG. 8, the sensor readout circuitry 100 may support a sub-set of the electrodes 302. However, it should be realized that, according to an alternative, the sensor readout circuitry 100 may support one of the electrodes 302 such that dedicated circuitry 100 is provided for each one of the electrodes 302.

Further, instead of being arranged in the portion of the carrier 406 intended to be inserted into the brain, the sensor readout circuitry 100 may be arranged in the base portion 508 so as to enable minimizing a size of a part the neural probe 500 to be inserted into the brain.

The electrodes 302 and the sensor readout circuitry 100 may still be arranged on a common substrate to ensure high signal integrity of the electrode signals received by the sensor readout circuitry 100.

In the above the inventive concept has mainly been described with reference to a limited number of examples. However, as is readily appreciated by a person skilled in the art, other examples than the ones disclosed above are equally possible within the scope of the inventive concept, as defined by the appended claims.

The invention claimed is:

1. A sensor readout circuitry comprising:
a delta-sigma modulator for converting an analog sensor input signal to a digital signal;
an input stage for receiving the analog sensor input signal, wherein the input stage comprises a transconductance amplifier comprising a pair of input transistors and a source degeneration resistor, a current mirror, and current sources, wherein the transconductance amplifier and the current mirror incorporate a flipped voltage follower, wherein a feedback signal from a digital-to-analog converter, DAC, of the delta-sigma modulator is received across the source degeneration resistor such that subtraction between the analog sensor input signal and the feedback signal is performed in the transconductance amplifier and mirrored by the current mirror to an output of the input stage;

wherein the transconductance amplifier comprises a first chopper between an input terminal for receiving the analog sensor input signal and an input transistor of the pair of input transistors for upmodulating the analog sensor input signal;

wherein the transconductance amplifier comprises a second chopper between the input transistor and the source degeneration resistor such that the analog sensor input signal is in baseband at a node in which the feedback signal is received;

wherein the transconductance amplifier comprises a third chopper before a connection of the transconductance amplifier to shared gates of the current mirror such that signals in the current mirror are in baseband;

whereby a chopping loop between the first, second and third choppers is formed including the input transistor and the current sources.

2. The sensor readout circuitry according to claim 1, wherein nodes in which the feedback signal is received are further connected to the current mirror having low impedance such that the circuitry is configured for DAC feedback current to flow into the current mirror and not be affected by chopping by the second chopper.

3. The sensor readout circuitry according to claim 1, wherein the delta-sigma modulator is a continuous-time delta-sigma modulator, CTDSM.

4. The sensor readout circuitry according to claim 1, wherein the first, second and third choppers are configured to operate at a chopping frequency between a Nyquist rate and a sample rate of the delta sigma modulator.

5. The sensor readout circuitry according to claim 1, wherein the input stage comprises a fourth chopper in a load of an output branch of the input stage.

6. The sensor readout circuitry according to claim 1, wherein the transconductance amplifier further comprises a bootstrapping circuitry, wherein the bootstrapping circuitry comprises a bootstrap transistor having a drain current controlled by a bootstrap current source, the bootstrap transistor further comprising a gate connected to a source of the input transistor and a source connected to a drain of the input transistor for reducing effect of gate-drain parasitic capacitance of the input transistor, wherein the bootstrap transistor and the bootstrap current source form part of the flipped voltage follower.

7. The sensor readout circuitry according to claim 6, wherein the bootstrapping circuitry further comprises a cascode transistor having a drain connected to the bootstrap current source, a gate connected to a fixed bias voltage and a source connected to the drain of the bootstrap transistor, wherein the cascode transistor forms part of the flipped voltage follower.

8. The sensor readout circuitry according to claim 6, wherein the bootstrapping circuitry is arranged within the chopping loop.

9. The sensor readout circuitry according to claim 6, wherein a bulk gate of the input transistor is connected to a source of the input transistor.

10. A biopotential signal sensor, comprising:
the sensor readout circuitry according to claim 1, and
at least one electrode configured for sensing a biopotential, wherein the at least one electrode is connected to the pair of input transistors of the sensor readout circuitry.

11. The biopotential signal sensor according to claim 10, wherein the sensor readout circuitry is arranged on a common substrate with the at least one electrode.

12. A neural probe, comprising:
the biopotential signal sensor according to claim 10, wherein the at least one electrode is arranged on a carrier configured for being inserted into the brain.

13. A method for readout of an analog sensor input signal; said method comprising:
receiving the analog sensor input signal at an input stage of a delta-sigma modulator;
chopping the analog sensor input signal by a first chopper before the analog sensor input signal is received at a gate of an input transistor of a transconductance amplifier of the input stage;
chopping a signal between input transistor and a source degeneration resistor by a second chopper such that a baseband signal is provided at a node of the source degeneration resistor;
following the analog sensor input signal by a flipped voltage follower of the transconductance amplifier and a current mirror such that a voltage across the source degeneration resistor follows the analog sensor input signal, wherein a signal in the flipped voltage follower is chopped by a third chopper before a connection to shared gates of the current mirror such that signals in the current mirror are in baseband;
receiving a feedback signal from a digital-to-analog converter of the delta-sigma modulator at the node of the source degeneration resistor;
subtracting the feedback signal from the analog sensor input signal by the transconductance amplifier and outputting a corresponding mirrored signal by the current mirror for quantizing of the analog sensor input signal by the delta-sigma modulator;
outputting a read out digital signal by the delta-sigma modulator.

14. The method according to claim 13, further comprising boosting input impedance of the input transistor of the transconductance amplifier by a bootstrapping circuitry.

* * * * *